(12) United States Patent
Wojnowicz et al.

(10) Patent No.: US 6,277,068 B1
(45) Date of Patent: Aug. 21, 2001

(54) LARYNGOSCOPE AND LAMP CARTRIDGE ASSEMBLY

(75) Inventors: Catherine Marie Wojnowicz; Stephen Edward Rink, both of Auburn; Thomas James Grant, Skaneateles, all of NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 09/408,604

(22) Filed: Sep. 30, 1999

(51) Int. Cl.[7] .................................................. A61B 1/267
(52) U.S. Cl. .......................... 600/199; 600/185; 362/158; 362/203
(58) Field of Search ..................................... 600/185, 199, 600/245, 184, 193, 223, 249; 362/572, 158, 203

(56) References Cited

U.S. PATENT DOCUMENTS

| | | | |
|---|---|---|---|
| 2,678,041 | * | 5/1954 | Thorburn et al. ................... 600/249 |
| 2,798,940 | * | 7/1957 | Alinat et al. ......................... 362/158 |
| 3,592,199 | * | 7/1971 | Ostensen .......................... 600/249 X |
| 4,273,112 | * | 6/1981 | Heine et al. .......................... 600/193 |
| 4,574,784 | * | 3/1986 | Soloway .............................. 600/193 |
| 4,669,449 | | 6/1987 | Bauman . |
| 4,679,547 | | 7/1987 | Bauman . |
| 4,694,822 | | 9/1987 | Bauman . |
| 4,729,367 | | 3/1988 | Bauman . |
| 4,815,451 | | 3/1989 | Bauman . |
| 4,958,624 | * | 9/1990 | Stone et al. .......................... 600/193 |
| 5,060,633 | * | 10/1991 | Gibson ................................ 600/193 |
| 5,178,131 | | 1/1993 | Upsher . |
| 5,461,552 | * | 10/1995 | Tillery .............................. 362/203 X |
| 5,501,651 | | 3/1996 | Bauman . |
| 5,542,905 | * | 8/1996 | Nussenbaum ................... 600/185 X |
| 6,013,026 | * | 1/2000 | Krauter et al. ....................... 600/193 |
| 6,036,639 | * | 3/2000 | Allred, III et al. .................. 600/193 |

* cited by examiner

Primary Examiner—Jeffrey A. Smith
(74) Attorney, Agent, or Firm—Wall, Marjama & Bilinski

(57) ABSTRACT

A cartridge assembly for a laryngoscope includes a housing which supports an axially movable miniature lamp assembly in the instrument handle and includes at least one sealing member which provides a fluid tight seal for the electrical contacts of the lamp assembly and the power supply of the laryngoscope regardless of the axial position of the lamp assembly.

14 Claims, 4 Drawing Sheets

LARYNGOSCOPE AND LAMP CARTRIDGE ASSEMBLY

FIELD OF THE INVENTION

The invention generally relates to medical diagnostic devices and more particularly to a laryngoscope or similar device having internal electrical contacts which are effectively sealed from dirt, debris, fluid and the like without requiring a seal for the entire instrument.

BACKGROUND OF THE INVENTION

Laryngoscopes are commonly used medical diagnostic instruments used to observe the throat area of a patient generally including a handle and a laryngeal blade which is removably attachable to the handle. The handle typically retains a power supply, such as a set of dry cell batteries, which energize a miniature lamp retained in an upper end of the handle. Light from the miniature lamp is directed to the end of the attached laryngeal blade in order to provide illumination and allow examination of the larynx. The laryngeal blade is constructed so as to push on the tongue during examination.

Instruments having light sources mounted in the upper end of the handle do not energize the light source until the laryngeal blade is attached. Typically, connection of the blade to the instrument handle draws the electrical contacts of the lamp assembly to the corresponding contacts of the power source.

In prior art devices, as described, it is possible for debris and body fluids to enter the blade and ultimately the hollow handle and the lamp assembly, thereby fouling the electrical contacts to the point in which premature replacement is required.

Certain prior art devices, such as those described in U.S. Pat. Nos. 4,669,449 and 4,694,822, each issued to Bauman, describe laryngoscopes having handles which are completely submersible. These devices have elaborate sealing means which include a tubular elastomeric body which is fitted in an upper portion of the handle, the body having additional provision for a pair of electrical terminals extending through the elastomeric body. Though these devices are quite useful, it is not always necessary to make the entire instrument handle fluid tight. On the other hand, it is highly desirous for the reasons stated above to protect the internal electrical contacts interconnecting the lamp assembly and the power source. Moreover, it is equally desirous to be able to maintain an effective seal regardless of whether or not the blade is actually attached to the handle.

SUMMARY OF THE INVENTION

It is a primary object of the present invention to overcome the above noted problems found in the prior art.

It is another primary object of the invention to provide an improved laryngoscope having internal electrical contacts that are effectively sealed from debris and/or fluids.

Therefore and according to a preferred aspect of the present invention, there is provided a laryngoscope comprising:

an instrument handle including a contained power supply;

a laryngeal blade releasably attachable to an upper end of said handle;

a lamp assembly including a miniature lamp biasedly attached to the upper end of said instrument handle such that attachment of said blade causes an electrical connection between said lamp assembly and said power supply to cause energization of said miniature lamp; and a lamp cartridge including a housing for retaining said lamp assembly with respect to said instrument handle and sealing means for sealing electrical contacts of said lamp assembly and said power supply from fluid and debris.

Preferably, the lamp carrier member is attached to the cartridge housing to allow axial movement between respective nonengaged and engaged positions relative to the electrical contacts contained within the cartridge housing. The lamp carrier member is biased in the non-engaged position until the laryngeal blade has been positively attached to the instrument handle. Blade attachment then causes the lamp carrier member to be shifted axially to the engaged position in which the electrical contacts of the lamp assembly and the power supply are brought into contact with one another.

The lamp carrier member retains the sealing member, preferably a rubberized quad ring, diaphragm, or O-ring, which engages the interior wall of the cartridge housing and provides a seal regardless of the axial position of the lamp carrier member.

According to another preferred aspect of the present invention, there is disclosed a lamp cartridge assembly comprising:

a housing having an interior;

a lamp assembly retained by said housing having an electrical contact contained within said housing interior; and sealing means for sealing the interior of the cartridge housing, including said electrical contact, from fluid and debris.

An advantage of the present invention is that an adequate fluid and dust tight seal is provided for the electrical contacts of the laryngoscope without requiring the entire handle to be sealed providing a cost effective and lightweight design.

Another advantage is that the seal is effective and reliable regardless of the axial position of the supported lamp carrier member. Furthermore, the components are each easily accessible for replacement as needed.

Another advantage of the present invention is that only external cleaning of the laryngoscope handle is required. That is, provision of a sealed cartridge assembly ensures that there is no need to concern oneself about the cleanliness of internalized areas.

Yet another advantage is that the described cartridge assembly can be cleaned as needed without the concerns of cleaning fluids entering the assembly and oxidizing or otherwise damaging the internal contacts so as to prevent proper function of the lamp assembly.

Yet another advantage is that provision of a seal as described prevents debris, body fluids, and/or cleaning fluids from penetrating the cartridge assembly and creating a potential area of bacterial growth. Consequently, there is no future risk of trapped fluid leakage from the cartridge, which previously could cause illness, contamination and undue stress of a patient.

These and other objects, features and advantages will become apparent upon reading the following Detailed Description which should be read in conjunction with the accompanying drawings.

DETAILED DESCRIPTION

The following discussion relates to a preferred embodiment of a lamp cartridge assembly in accordance with the present invention. Throughout the course of this discussion certain terms including "top", "upper", "lower", "front", "back" and the like are used to provide a frame of reference with regard to the drawings. These terms, however, are not intended to be limiting of the claimed invention.

Figure 1:
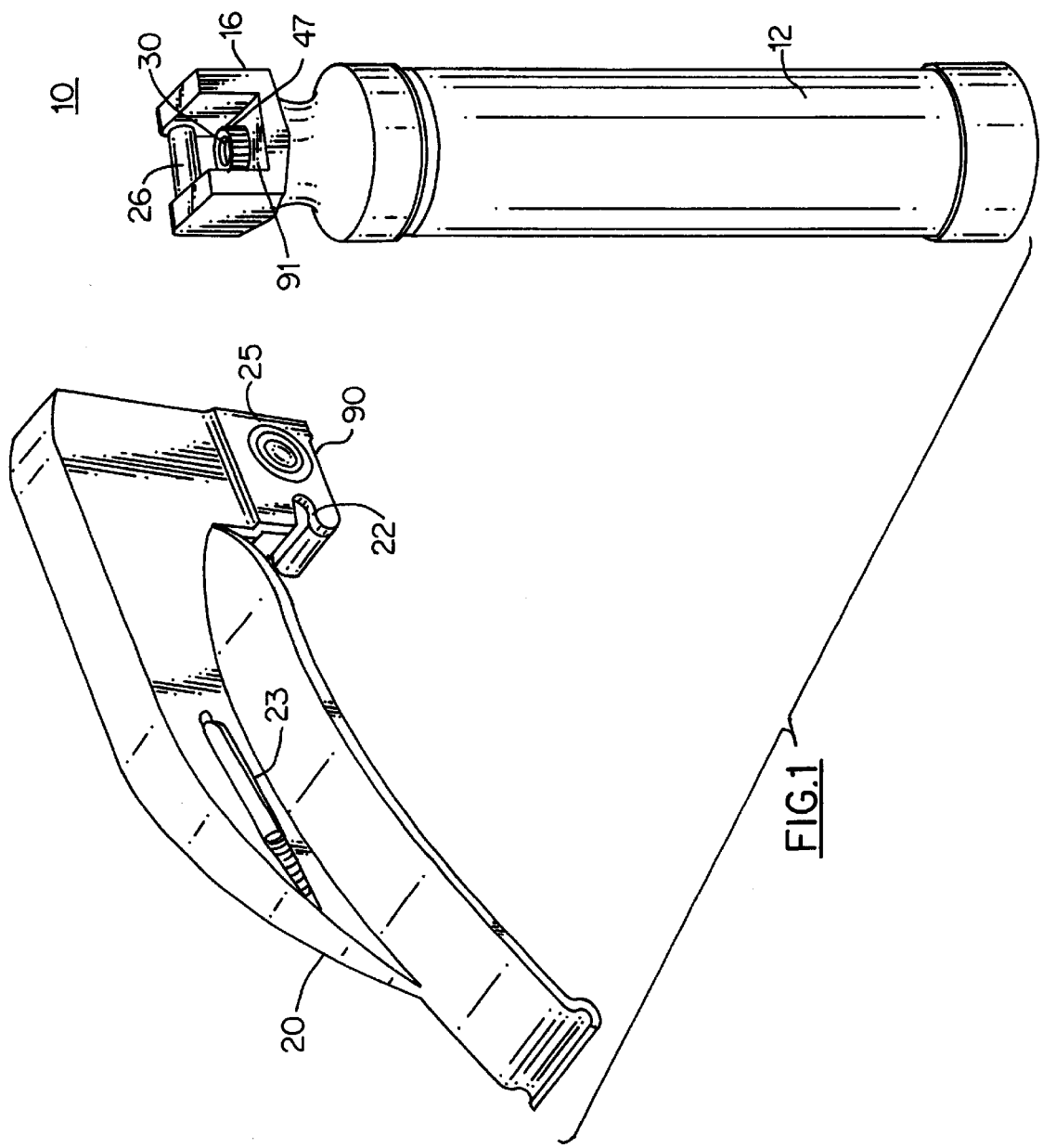
FIG. 1 is a front perspective view of a laryngoscope.
Figure 4:
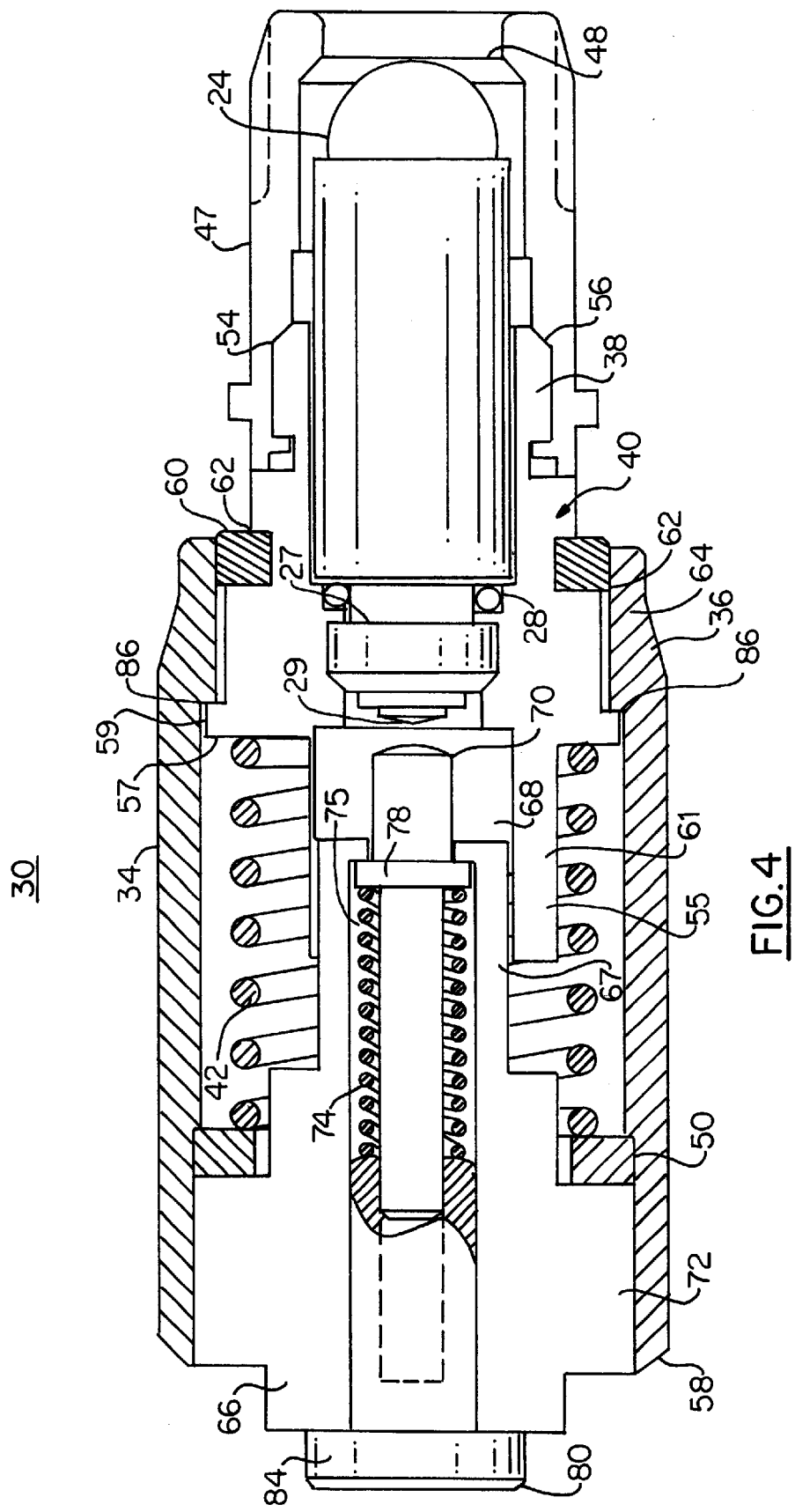
FIG. 4 is a sectioned view of the lamp cartridge assembly of FIGS. 2 and 3 with the lamp assembly disposed in an non electrically engaged position.

Turning to FIG. 1, there is shown a laryngoscope 10 which includes a hollow cylindrical instrument handle 12 having an interior sized for containing a pair of dry cell batteries (not shown). The batteries are typically stacked end to end and are used to power a lamp assembly 40, identified in FIG. 4, retained by a lamp cartridge assembly 30 (partially shown in FIG. 1) which is fitted into an upper end 16 of the handle 12. In brief, light emitted from the lamp assembly 40, FIG. 4, is directed to a light pipe containing a bundle of optical fibers 23 disposed in a laryngeal blade 20 which is releasably connected to the upper end 16 of the instrument handle 12. More particularly and according to this specific embodiment, the laryngeal blade 20 includes a slotted portion 22 at an attachment end 25 thereof which is fitted onto a lug 26 provided at the upper end 16 of the instrument handle 12. Further details relating to the laryngeal blade 20 and attachment of the blade to the instrument handle 12 are as described, for example, in commonly assigned U.S. Ser. No. 09/257,762, filed Feb. 25, 1999, now U.S. Pat. No. 6,013,026, the entire contents of which are herein incorporated by reference.

Figure 2:
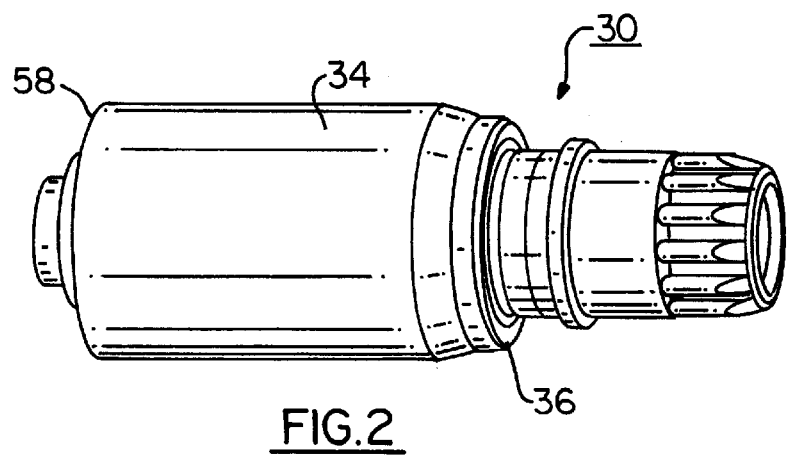
FIG. 2 is a perspective view of a lamp cartridge assembly used in the laryngoscope of FIG,. 1 and made in accordance with a preferred aspect of the invention.

Turning to FIG. 2, the lamp cartridge assembly 30 includes a cartridge housing 34 made from brass or other suitable material, the housing having a pair of opposing ends including an upper or top end 36 and a lower or bottom end 58. Each of the upper and lower ends 36, 58 include respective openings 44, 46, each shown in FIG. 3, defining a cartridge interior sized for receiving a number of components. These components will now be described in greater detail.

Figure 5:
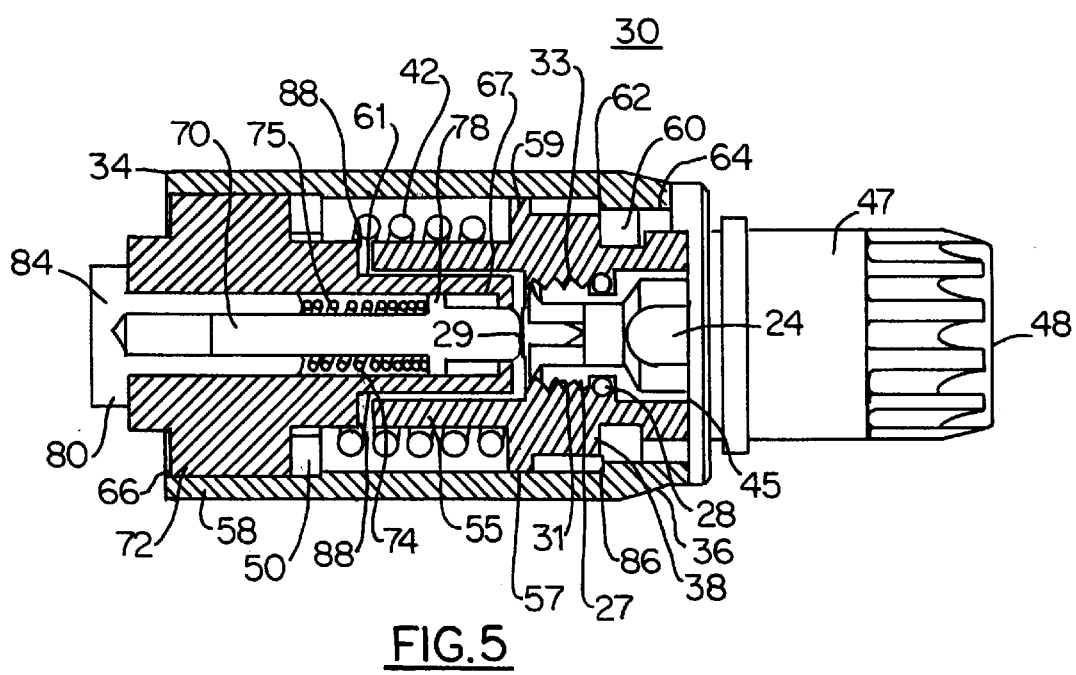
FIG. 5 is the sectioned view of the lamp cartridge assembly of FIG. 4 with the lamp assembly in an electrically engaged position.
Figure 3:
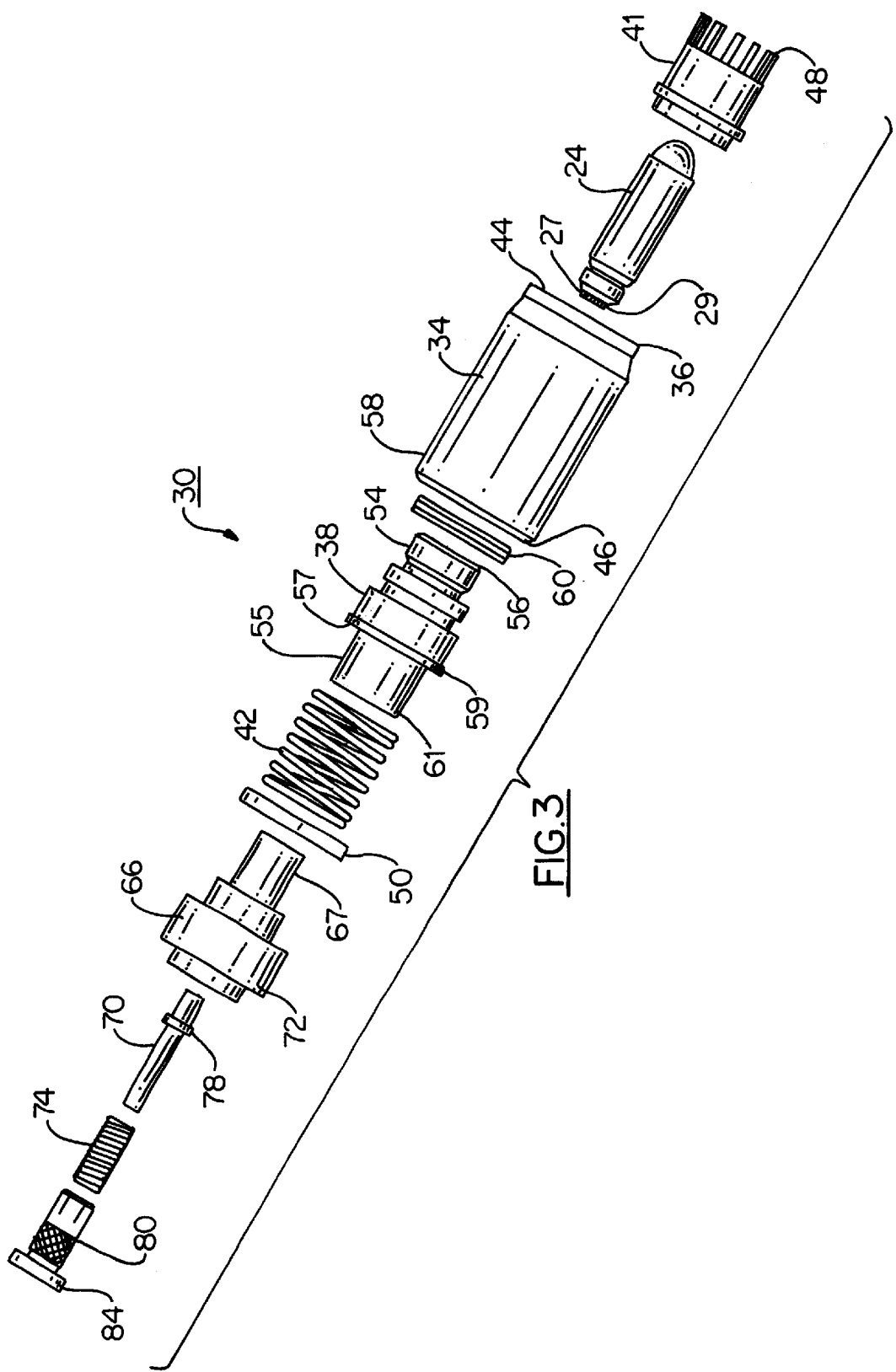
FIG. 3 is an exploded view of the lamp cartridge assembly of FIG. 2.

Referring to FIGS. 3–5, the lamp assembly 40 is slidingly fitted into the upper end 36 of the cartridge housing 34, the assembly including a lamp carrier member 38 having a top opening 45, FIG. 5, into which a miniature lamp 24 is threadingly fitted. An O-ring 28, shown only in FIGS. 4 and 5, is provided to assist in sealing the electrical contacts 29 at the base 27 of the miniature lamp 24 between respective threaded portions 31, 33. When engaged therewith, a portion of the miniature lamp 24 projects a predetermined distance from the upper end 56 of the lamp carrier member 38. A plastic plunger or sleeve 47 engaged onto a set of external threads 54 at the upper end 56 of the lamp carrier member 38 protects the miniature lamp 24, the plunger having a top opening 48, permitting light to exit therefrom.

The bottom end 61 of the lamp carrier member 38 includes a cylindrical projecting portion 55 having a diameter which is smaller than the remainder of the carrier member, including a annular shoulder 59 abutting the upper end of the projecting portion.

An insulating body 66 made from plastic, phenolic, or other suitable material is press fitted and/or epoxied into the bottom end 58 of the cartridge housing 34, the body having an upper end 67 which is sized to fit into a recess 68 defined in the projecting portion 55 of the lamp carrier member 38. A lower end 72 of the insulating body 66 effectively fills the bottom end 58 of the cartridge housing 34 with the exception of a center through opening 75 containing a contact pin 70 biased into a first projecting position by an internal spring 74 supported between an upper shoulder 78 of the contact pin and a plug 80, the upper end of which is tightly engaged into the center opening 75 of the insulating body 66 and having a head 84 which extends outwardly from the lower end 72 of the insulating body.

An axial portion of a biasing spring 42 is fitted about the exterior of the cylindrical projection 55 of the lamp carrier member 38 with the upper end of the spring bearing against the bottom surface 57 of the annular shoulder 59. The lower end of the biasing spring 42 engages against a brass washer 50 disposed onto a shoulder intermediately disposed between the upper and lower ends 67, 72 of the insulating body 66.

Referring to FIG. 5, the respective outer dimensions of the lamp carrier member 38 and the inner diameter of the cartridge housing 34 permit axial movement of the lamp carrier member. The interior wall 64 of the cartridge housing 34 is narrowed immediately adjacent the upper end 36 in comparison with the remainder of the interior, the wall being outwardly stepped at an axial portion and forming a stop 86 when engaged by the annular shoulder 59 of the lamp carrier member 38. A similar stop is provided in the opposing axial direction when the bottom of the cylindrical projecting portion 55 of the lamp carrier member 38 engages an abutment 88 of the insulating body 66.

As most clearly illustrated in FIGS. 4 and 5, the lamp carrier member 38 includes a circumferential notch 62 into which a rubberized sealing ring 60 is positioned, the ring engaging the interior wall 64 of the cartridge housing 34 at the upper end 36 and preventing fluid or debris from entering the interior of the cartridge housing. According to this embodiment, the ring member 60 is defined by a quad (4 sided) configuration which remains in engagement with the interior wall 64 over the entire range of axial positions of the lamp carrier member 38.

FIG. 4 shows the fully assembled cartridge assembly 30 prior to the attachment of the laryngeal blade 20, FIG. 1. Prior to blade attachment, the lamp carrier member 38 is fully acted upon by the biasing force supplied by the spring 42 which positions the electrical contacts 29 of the miniature lamp 24 away from the contact pin 70. The sealing ring member 60 and the press fitted insulating body 66 protect the interior of the cartridge housing 34 and provide a substantial dust and fluid tight seal. As noted above, the annular shoulder 59 engages the stop 86, defining a first or electrically unengaged position.

Referring now to FIGS. 1 and 5, and in operation, the laryngeal blade 20 is attached to the upper end 16 of the hollow instrument handle 12 by snapping the slotted portion 22 onto the lug 26 and rotating the section 22 such that the bottom edge 90 of the blade 20 is parallel to the handle neck surface 91. Engagement of the blade 20 in this manner causes the attachment portion 25 to bear upon the projecting plastic plunger 47, thereby axially shifting the lamp carrier member 38 against the biasing force supplied by the spring 42 to an electrically engaged position. In this "engaged" position, the electrical contacts 29 of the miniature lamp 24 are driven into intimate contact with the contact pin 70. This engagement causes the contact pin 70 to shift axially against the biasing force of spring 74 and completing the electrical connection, the plug 80 being in engagement with the batteries (not shown) in the handle interior to cause energization of the miniature lamp 24.

In the meantime, and regardless of the axial position of the lamp carrier member 38, the rubberized sealing ring 60 prevents fluid or other debris from entering the interior of the cartridge housing 34. According to the preferred embodiment, the sealing ring 60 is a quad ring having four (4) sides which maintain their position for wiping. The ring has a pair of opposing wiping surfaces as compared to a single wipe of an O-ring which is somewhat effective, but which makes this configuration more desirable. A diaphragm could also be substituted.

The entirety of the cartridge assembly 30 can be removed through the bottom of the handle 12, as needed, for cleaning.

PARTS LIST FOR FIGS. 1–5

10 laryngoscope
12 hollow instrument handle
16 upper end
20 laryngeal blade
22 slotted portion
23 light pipe containing optical bundle
24 miniature lamp
25 attachment end
26 lug
27 lamp base
28 O ring
29 electrical contacts
30 lamp cartridge assembly
31 threaded portion
33 threaded portion
34 cartridge housing
36 upper end
38 lamp carrier member
40 lamp assembly
42 spring
44 opening
45 top opening
46 opening
47 plastic plunger
48 plunger opening
50 washer
54 external threads
55 cylindrical projecting portion
56 upper or top end
57 bottom surface
58 lower or bottom end
59 annular shoulder
60 sealing ring
61 bottom end
62 circumferential notch
63 center opening
64 interior wall
66 insulator body
67 upper end
68 recess
70 pin, contact
72 lower end (body)
74 spring
75 center opening
78 upper shoulder
80 plug
84 head
86 stop
88 abutment
90 bottom edge
91 handle neck surface Though the above invention has been described in terms of a single embodiment, it be appreciated that variations and modifications are possible within the scope of the invention as claimed herein.

We claim:

1. A lamp cartridge assembly for a hand-held laryngoscope, said laryngoscope having an instrument handle, said cartridge assembly comprising:

a cartridge housing nonsealingly disposed within the interior of said instrument handle, said cartridge housing having an interior;

a lamp assembly retained by said cartridge housing, said lamp assembly having at least one electrical contact contained within the interior of said cartridge housing; and sealing means for sealing only the interior of the cartridge housing, including said at least one electrical contact, from fluid and debris, said lamp cartridge assembly being releasably attachable relative to said instrument handle without sealing the interior of the instrument handle.

2. A lamp cartridge assembly as recited in claim 1, including biasing means for biasing said lamp assembly in a first axial position within said cartridge housing in which a first electrical contact is not electrically engaged.

3. A lamp cartridge assembly as recited in claim 2, wherein said lamp assembly is axially movable within said cartridge housing between said first axial position and a second axial position in which the first electrical contact is engaged with at least one other electrical contact contained in the cartridge housing.

4. A lamp cartridge assembly as recited in claim 3, wherein said lamp assembly includes a miniature lamp and a lamp carrier member, said lamp carrier member being retained within said cartridge housing.

5. A lamp cartridge assembly as recited in claim 4, wherein said sealing means includes a sealing ring member attached to said lamp carrier member, said sealing ring member being in contact with an interior wall of said cartridge housing regardless of the axial position of said lamp assembly.

6. A lamp cartridge assembly as recited in claim 5, wherein said sealing ring member has a quad-like cross section.

7. A laryngoscope comprising:

an instrument handle including a contained power supply;

a laryngeal blade releasably attachable to an upper end of said instrument handle; and a lamp cartridge assembly including a lamp assembly, said lamp assembly including a miniature lamp biasedly attached to the upper end of said instrument handle such that attachment of said laryngeal blade causes an electrical connection between said lamp assembly and said power supply to cause energization of said miniature lamp, and in which said lamp cartridge assembly further includes a cartridge housing for retaining said lamp assembly, said lamp cartridge assembly including sealing means for sealing only the interior of said cartridge housing including electrical contacts of said lamp assembly from fluid and debris, said lamp cartridge assembly being nonsealingly engaged with said instrument handle.

8. A laryngoscope as recited in claim 7, wherein said lamp assembly includes a carrier member which supports said miniature lamp, said carrier member being movable between first and second axial positions within said cartridge housing wherein electrical contact between said lamp assembly and said power supply is achieved in said second axial position.

9. A laryngoscope as recited in claim 8, wherein said sealing means includes a sealing ring member, said cartridge housing further containing electrical contacts for the power supply contained within said instrument handle.

10. A laryngoscope as recited in claim 9, in which said sealing ring is disposed on said carrier member for engaging an interior wall of said cartridge housing.

11. A laryngoscope as recited in claim 9, wherein said sealing ring has a quad-like construction.

12. A laryngoscope as recited in claim 9, wherein said cartridge housing includes an opening through which said miniature lamp protrudes, said laryngoscope including a plunger which covers said lamp, said plunger having an opening to allow light to pass therethrough and in which said plunger engages said laryngeal blade when attached to said handle to move said carrier member from the first to the second axial position.

13. A laryngoscope as recited in claim 12, including biasing means for biasing said carrier member in said first axial position.

14. A laryngoscope as recited in claim 13, wherein said biasing means includes a spring retained in said cartridge housing for biasing said lamp assembly into said first axial position.

* * * * *